(12) United States Patent
Yuasa et al.

(10) Patent No.: US 12,132,986 B2
(45) Date of Patent: Oct. 29, 2024

(54) COMPUTER VISION SYSTEM USED IN VEHICLES

(71) Applicant: Avanti R&D, Inc., Torrance, CA (US)

(72) Inventors: Go Yuasa, Rancho Palos Verdes, CA (US); Michael J Ramirez, Torrance, CA (US)

(73) Assignee: AVANTI R&D, INC., Torrance, CA (US)

( * ) Notice: Subject to any disclaimer, the term of this patent is extended or adjusted under 35 U.S.C. 154(b) by 132 days.

(21) Appl. No.: 18/078,904

(22) Filed: Dec. 9, 2022

(65) Prior Publication Data

US 2023/0188836 A1 Jun. 15, 2023

Related U.S. Application Data

(60) Provisional application No. 63/288,620, filed on Dec. 12, 2021.

(51) Int. Cl.
| | |
|---|---|
| *H04N 23/65* | (2023.01) |
| *B60R 16/033* | (2006.01) |
| *G01N 33/00* | (2006.01) |
| *G06V 10/26* | (2022.01) |
| *G06V 20/58* | (2022.01) |

(Continued)

(52) U.S. Cl.
CPC ......... *H04N 23/651* (2023.01); *B60R 16/033* (2013.01); *G01N 33/0063* (2013.01); *G06V 10/26* (2022.01); *G06V 20/58* (2022.01); *H04N 23/61* (2023.01); *H04N 23/667* (2023.01); *G06V 40/173* (2022.01)

(58) Field of Classification Search
CPC .... H04N 23/651; H04N 23/61; H04N 23/667; H04N 23/611; H04N 23/617; B60R 16/033; G01N 33/0063; G06V 20/58; G06V 20/56; G06V 40/173
See application file for complete search history.

(56) References Cited

U.S. PATENT DOCUMENTS 8,026,945 B2 * 9/2011 Garoutte ................. H04N 5/76
348/208.1
9,418,320 B2 * 8/2016 Chang ...................... G06T 7/337
(Continued)

*Primary Examiner* — Timothy R Newlin
(74) *Attorney, Agent, or Firm* — Law Office of Katsuhiro Arai

(57) ABSTRACT

A computer vision system used for a vehicle having a camera system including an AI camera having a capability of recognizing 1) surrounding environment, 2) moving objects at the surrounding environment, 3) a parking location and direction, and a capability of setting a non-recognition area, wherein numbers of the moving objects passing through the non-recognition area are more than a predetermined number in a predetermined period, a controller including software programs for controlling functions of the AI camera, a battery and a server designed to communicate to the camera system for processing the data from the camera system via the communication device, wherein the software programs include a function for allowing the AI camera to recognize the surrounding environment between the parking location of the vehicle to the non-recognition area, and wherein the software programs further include a function for controlling power from the battery to the camera system.

15 Claims, 1 Drawing Sheet

(51) Int. Cl.
*H04N 23/61* (2023.01)
*H04N 23/667* (2023.01)
*G06V 40/16* (2022.01)

(56) References Cited

U.S. PATENT DOCUMENTS

| | | | | |
|---|---|---|---|---|
| 10,528,818 | B1* | 1/2020 | Rao | G06V 20/40 |
| 10,930,145 | B2 | 2/2021 | Yuasa | |
| 10,940,790 | B1* | 3/2021 | Mazuir | B60Q 3/80 |
| 11,086,335 | B2* | 8/2021 | Kim | G06V 20/58 |
| 11,373,447 | B2 | 6/2022 | Nagata et al. | |
| 11,708,076 | B2* | 7/2023 | Fent | G06V 20/588 |
| | | | | 701/36 |
| 11,792,507 | B1* | 10/2023 | Di Febbo | H04N 23/90 |
| | | | | 348/262 |
| 2003/0210807 | A1* | 11/2003 | Sato | G08G 1/165 |
| | | | | 382/104 |
| 2004/0057600 | A1* | 3/2004 | Niwa | G06T 7/254 |
| | | | | 382/103 |
| 2006/0013438 | A1* | 1/2006 | Kubota | G06V 20/58 |
| | | | | 382/103 |
| 2010/0232646 | A1* | 9/2010 | Takeuchi | H04N 23/61 |
| | | | | 382/103 |
| 2013/0278774 | A1* | 10/2013 | Fujimatsu | H04N 7/185 |
| | | | | 348/159 |
| 2014/0146172 | A1* | 5/2014 | Kajitani | H04N 23/611 |
| | | | | 348/143 |
| 2014/0218529 | A1* | 8/2014 | Mahmoud | H04N 23/667 |
| | | | | 348/148 |
| 2015/0143913 | A1* | 5/2015 | Adams | G06V 20/52 |
| | | | | 382/104 |
| 2016/0103111 | A1* | 4/2016 | Griffin | B60N 2/002 |
| | | | | 73/25.01 |
| 2016/0257198 | A1* | 9/2016 | Buttolo | B60K 35/10 |
| 2016/0280133 | A1* | 9/2016 | Salomonsson | B60T 7/22 |
| 2016/0364619 | A1* | 12/2016 | Ogata | G06T 7/50 |
| 2017/0006228 | A1* | 1/2017 | Takayanagi | H04N 23/6815 |
| 2017/0151918 | A1* | 6/2017 | Boesen | B60R 16/037 |
| 2017/0332016 | A1* | 11/2017 | Miyakawa | H04N 5/772 |
| 2018/0032217 | A1* | 2/2018 | Kim | G06F 18/24 |
| 2019/0019031 | A1* | 1/2019 | Yun | G06T 7/251 |
| 2019/0339706 | A1* | 11/2019 | Batur | G05D 1/0223 |
| 2019/0370609 | A1* | 12/2019 | Akiyama | G06V 10/454 |
| 2019/0392232 | A1* | 12/2019 | Ma | H04N 23/695 |
| 2020/0043513 | A1* | 2/2020 | Atkinson | H04N 23/667 |
| 2020/0082561 | A1* | 3/2020 | Karonchyk | G06T 7/74 |
| 2020/0106999 | A1* | 4/2020 | Okazaki | H04N 23/75 |
| 2020/0364885 | A1* | 11/2020 | Latapie | G06T 7/174 |
| 2021/0245711 | A1* | 8/2021 | Nagata | H04N 7/181 |
| 2021/0271257 | A1* | 9/2021 | Watanabe | G06F 18/24 |
| 2021/0327011 | A1* | 10/2021 | Bielby | G06V 40/172 |
| 2022/0019767 | A1* | 1/2022 | Burk | G06F 18/217 |
| 2022/0063604 | A1* | 3/2022 | Okano | G06V 20/64 |
| 2022/0207278 | A1* | 6/2022 | Nagata | H04N 5/77 |
| 2022/0242352 | A1* | 8/2022 | Nagata | B60R 21/01534 |
| 2022/0301427 | A1* | 9/2022 | Ueno | G08G 1/096783 |
| 2023/0091062 | A1* | 3/2023 | Challa | G06V 20/582 |
| | | | | 382/104 |
| 2023/0386259 | A1* | 11/2023 | Chakradhar | G06V 20/52 |
| 2024/0135724 | A1* | 4/2024 | Bhanushali | G06V 40/10 |

* cited by examiner

COMPUTER VISION SYSTEM USED IN VEHICLES

This non-provisional application claims priority from U.S. Provisional Patent Application Ser. No. 63/288,620 filed, Dec. 12, 2021, the contents of which are incorporated herein by reference in its entirety.

TECHNICAL FIELD OF THE INVENTION

The present invention relates to a technical field of an apparatus and a method for improving the power consumption of computer vision systems used in vehicles.

BACKGROUND OF THE INVENTION

In-vehicle cameras are usually powered by a vehicle's power supply or a car battery. Therefore, there is a concern about battery drain. Although hardware manufacturers are working on ways to reduce the power consumption of the in-vehicle camera itself, the development of software for controlling the camera system is also required to further reduce the power consumption of the in-vehicle battery by shortening camera shooting time according to the situation of the vehicle.

SUMMARY OF THE INVENTION

In an embodiment of this invention, a method is implemented where an AI-powered camera system learns its location and environment, such as vehicles and people (here referred to as objects) passing around the vehicle and avoids unnecessary power consumption by reducing processing of false positive detection of the objects. Where an AI-powered camera, also referred to as an "AI camera", is defined as a camera capable of additional onboard processing of its image frames without the need for assistance from an external processor to output information (its "intelligence"), in addition to the image frames, including but not limited to: objects detected in the image frames, objects recognized in the image frames, etc. The AI camera may or may not have the ability to have parameters or its method of intelligence processing modified.

In one embodiment, a computer vision system used for a vehicle includes a camera system having an AI camera installed in or on the vehicle having a capability of recognizing 1) the surrounding environment, 2) moving objects including vehicles in the surrounding environment, 3) the parking location of and the parking direction of the vehicle, and a capability of setting a non-recognition area in the surrounding environment within which the number-of the moving objects passing through the non-recognition area are more than a predetermined threshold number in a predetermined period, a communication device for communicating data from the computer vison system, a controller including software programs for controlling functions of the AI camera and the communication device, a battery for supplying power to the camera system; and a server designed to communicate with the camera system for processing the data from the camera system via the communication device, wherein the software programs include a function for allowing the AI camera to recognize the surrounding environment between the parking location of the vehicle to the non-recognition area.

In the case of a vehicle parked facing a street, where objects are constantly passing by on the street, the camera system learns the location and relative position of the vehicle with respect to the street. In this case, the camera system understands the vehicle's position and parking direction and sets a recognition area to include recognizable objects that are located in an area extending from a spatial plane beginning at the border of the vehicle's body to a spatial plane just in front of the street and does not include recognizable objects in the street and beyond.

In order to set the non-recognition area, it is necessary to count the number of the moving object per certain time period. In general, the number of the moving objects on the street depends on the time of day, so in this embodiment, the certain time period can be variable.

The camera system uses background removal technology (technology that extracts only objects which do not affect the ability to recognize the recognition area, such as people, by removing the background), which enables the camera system to know that the vehicle is parked in the same place even if the vehicle moves and returns to the same location. Therefore, the AI camera can reduce the process of calculating the recognition area every time.

It is possible to use satellite positioning system such as GPS to determine whether the car has been parked in the same location. However, since the positional accuracy of GPS typically used in current and older vehicles is ±10 m to 50 m, the error in satellite positioning accuracy is too large to identify the visual field of the camera.

In a vehicle with multiple cameras installed outside the vehicle (on the vehicle body) and inside the vehicle cabin, power consumption may be wasted if all cameras are always turned on, and it cannot be said that they are effectively utilized. Therefore, in this embodiment, the power consumption is reduced by a method that can be equipped with a mode that takes the following steps as described below.

DETAILED DESCRIPTION OF THE INVENTION

Embodiment 1

System Configuration

Figure 1:
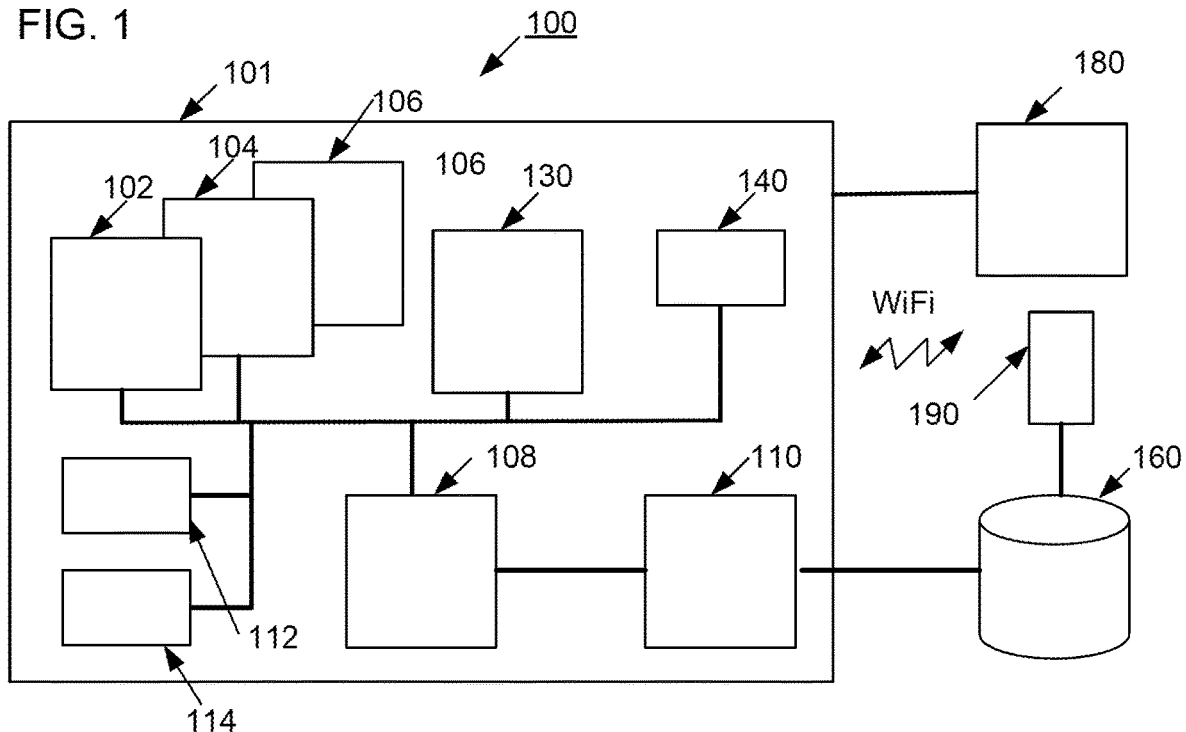
FIG. 1 illustrates a computer vision system configured by a camera system used operated by a battery in a vehicle and a server.

FIG. 1 illustrates a computer vision system 100 configured by a camera system 101 used under a battery 180 in a vehicle and a server 160 being installed outside of the computer vision system. The camera system 101 includes AI cameras 102, 104 and 106, a sound sensor 112, a $CO_2$ sensor 114, a camera 130 having a higher resolution than that of AI cameras 102, 104 and 106, a Satellite Positioning System or Global Positioning system (GPS) 140, a communication interface 110 and a controller 108 for controlling functions of the camera system 101. A car battery 180 supplies power to the camera system 101. The computer vision system 100 automatically tunes and continuously updates the camera system 101. Data from the camera system 101 is communicated to a server 160 where the data is analyzed, and updates are communicated back to the camera system 101 under appropriate conditions via the communication interface 110. The camera system 101 is installed in multiple vehicles, so a plurality of camera systems is linked to the server 160 via the communication interface 110. A cellular phone or other cellular communication device 190 linked to sever 160 via network. Cellular phone 190 also is arranged to be linked with camera system via Bluetooth or WiFi network. Server having no-link to cellular phone system may be used in another embodiment of this invention.

Sound sensor 112 is designed to capture sound signals inside and/or outside the vehicle. A carbon dioxide concentration sensor 114 is designed to measure carbon dioxide concentration in the air inside and/or outside of the vehicle. Each camera system 101 is equipped with initial settings derived from initial lab/bench/server testing. The camera system 101 has capability, under certain circumstances, to record and send raw, unprocessed data, including camera image frames, to the server 160. If environment parameters are different from known environment information, some recording of the environment is saved (stored and uploaded to the server 160 later also possible).

Server Functions

Firstly, initial file settings of the computer vision system 101 including data of location and direction of the vehicle having the camera system 101 are performed based on Satellite Positioning System or GPS (Global Positioning System) 140 location. Then, when the camera system 101 automatically tunes and updates itself the settings, files and geotagged data are uploaded from each vehicle as a distributed node including server 160. Other vehicles also transmit the same information through distributed nodes including to the server 160.

As described above, upon startup, each vehicle linked to the node records parameters of its environment including the data of location and direction of the vehicle. If environment parameters are different from known environment information, some recording of the environment is saved (stored and uploaded later also possible).

Then, server 160 evaluates and analyses the data, including but not limited to location and direction of the vehicle, timestamp of the data, weather reports, etc. and calculate new "best" parameters. Outside data is also tagged to the output of the parameters. If data from new vehicles are consistent but different from known values on the server for the camera system's location and direction, then the area is designated as a "collection" zone. Future vehicles in the "collection" zone, in addition to computed data, will send collected raw data to the server 160 for inclusion in the AI camera and controller improvement process. Parameters are then downloaded to the camera systems that enter the geolocation area where the original camera was located. The server 160 can also update camera system 101 that are experiencing similar scene/lighting conditions as those in the above-mentioned "collection' zone. Overall system management software can continuously update and optimize for varying and new environments that could not possibly be included in the original development/deployment.

As described previously, a carbon dioxide ($CO_2$) concentration sensor 114 ($CO_2$ sensor) is designed to measure carbon oxide concentration in the air inside and/or outside of the vehicle. Each camera system 101 is equipped with initial settings derived from initial lab/bench/server testing. When, environment parameters are different from known environment information, some recording of the environment is saved (stored and uploaded to the server 160 later also possible).

After sufficient data from a "collection" zone is obtained, server 160 creates improved programs for the controller and/or AI cameras and/or settings files for the zone previously labeled as a "collection" zone, and downloads updated settings files and/or programs to camera systems in that zone and which may enter the zone in the future. The server 160 can also update camera systems 101 that are experiencing similar scene/lighting conditions as those in the above-mentioned "collection" zone. Overall system management software can continuously update and optimize for varying and new environments that could not possibly be included in the original development/deployment.

AI Camera Functions

AI cameras 102, 104 and 106, set inside the vehicle, being, interior cameras from now on in this embodiment, are designed to be turned on when the exterior camera including an AI camera (not seen in FIG. 1) detects an intruder. Otherwise, the interior cameras are turned off Immediately after parking, the interior cameras can be turned on for a certain period in consideration of children or pets that are left behind. On the other hand, the exterior cameras including an AI camera outside the vehicle (not seen in FIG. 1) shall be turned off for a certain period, immediately after parking, in consideration of unwanted detection of the user occupants or a driver of the vehicle getting out of the vehicle and moving around. In this specification, turning the camera on or off also includes the meaning that the function of switching the AI camera between standby mode (a power save mode) and normal operation mode (a power on mode).

However, if an AI camera inside the vehicle detect that children or pets that are left behind even though the doors are locked, it may be necessary to monitor the surrounding situation, an AI camera outside the vehicle can also be turned on to watch around the vehicle. In other words, the software programs further include a function for turning on or off power the AI camera inside the vehicle or an AI camera outside the vehicle independently when the AI camera outside the vehicle captures a person located within a certain distance of the vehicle for a predetermined period. In another embodiment, the software programs further include a function for turning on or off power the AI camera inside the vehicle or the AI camera outside the vehicle independently for a predetermined period starting from time an occupant leaves the vehicle.

It is possible that the AI cameras 102, 104 and 106 cannot identify objects for a certain period of time due to lighting conditions like direct sunlight. In such a case, the camera system 101 learns when to turn off the camera using the controller 108 (off-time) in order to save power based on historical information (such as the previous day's information) where the angle of the sun does not differ greatly depending on the season or weather. The same trend is expected for several days as the angle of incidence of the sun depends on the season. If the vehicle stops at the same direction and position when using sensors such as gyro or GPS (Global Positioning System 140: a location sensor), the corresponding AI camera will be turned off to save power consumption. Following is an embodiment of this case described above. The computer vision system further includes a location sensor for detecting a parking location and a parking direction of the vehicle (GPS 140), the location senor sensor that is linked to the controller. The software programs further include a function for checking whether there is data including the same parking location and parting direction in a past. Then, the software programs turn off power supply from the battery to the AI camera to save power consumption of the battery when there is the same data and the AI camera cannot recognize any one of surrounding environment, moving objects and a parking location of the vehicle.

When the vehicle is moved, the camera system 101 may cancel the above-mentioned off time if it judges the angle of incidence of the sun changes and no longer impedes the AI cameras 102, 104, 106 from performing object identification or some other function desired for the system's geo-spatial location. The system assesses the environment at its new stopped position or refers to historical data. If the vehicle is equipped with multiple AI cameras, each camera should be able to turn on and off on its own.

The AI camera used in an embodiment of this application is generally designed with low resolution and low number of colors to reduce power consumption. As a result, it is difficult to identify a person's face in the image frame, and it may be difficult for the police to put out an APB (all-points bulletin) based on an image obtained from said AI camera.

In recent years, more and more vehicles are equipped with safety functions such as lane keeping assist and advanced cruise control. In order to realize these functions, vehicles equipped with high-precision cameras are becoming more and more common.

However, high-resolution cameras generally consume a lot of power and are not suitable for use in a stationary vehicle for applications that aim to reduce power consumption, such as an embodiment of this application as described in this specification. Firstly, when the camera system 101 recognizes that a suspicious person is approaching the vehicle, or that a suspicious person has been in the vicinity of the vehicle for a certain period, it triggers the high-resolution camera described above to record or take pictures.

A suspicious person is defined here as a person who has stopped for a certain period or longer within a certain distance from the vehicle, for example, a person who enters a 1-meter radius and stops for 5 seconds or longer. The distance and time can be set and changed dynamically based on multiple factors including scene and lighting analysis performed by the camera system 101 either on the controller 108 or on one or more of the AI cameras if the hardware is capable. In this way, in an embodiment of this application, it is possible to acquire high-resolution images while reducing power consumption of the battery 180 by combining a high-resolution camera and a camera system 101 with ultra-low-power AI camera(s).

Although we are describing here the use of a high-resolution camera that is already integrated in the vehicle, a dedicated high-resolution camera can be equipped for this purpose. The ultra-low-power AI camera can function as a switch or a trigger device so that the high-resolution camera, which consumes a lot of power, does not have to be used at all times. Incidentally, the system can also take actions such as making a warning sound or sending a warning message to the vehicle owner when it recognizes a suspicious person.

In addition to the above, since the camera system can track the direction of movement of the object, the following conditions can also be used to identify a suspicious person: the vector of the person's movement is calculated as directed toward part of the vehicle, the person has approached the vehicle at a certain speed, the body (or face) is facing the vehicle, or the person has stopped within a certain distance for a certain period with the body facing the vehicle. This analysis and determination could be made on the controller 108 or on a combination of one or more AI cameras if the hardware is capable, whichever combination thereof which results in the lowest power consumption. The movement criteria could also be updated over time for behavior patterns that are desired to be categorized as suspicious.

Additional object type detections and calculated distances could also be input into the analysis for classifying a person as suspicious. For example, if another vehicle is detected as approaching to the vehicle quickly, followed by rapid movement toward the vehicle of a person, this scenario or others like it could be part of the software program to be recognized as suspicious.

For a suspicious person, there is a possibility that the vehicle owner, the owner's family members, or acquaintances may frequently come and go in the vicinity of the vehicle (within the detection range described above). It is not user-friendly to issue a warning each time this happens. To avoid this, a face recognition technology could be used to memorize faces, but as mentioned above, low-power AI cameras may not be able to recognize faces due to their low resolution and low number of colors. In such a case, a unique WiFi, Bluetooth, or other transceiver ID (MAC address, etc.) from a smartphone, cellular phone 190, or other personal electronics device with transceiver module that can be individually identified as illustrated in FIG. 1 owned by the vehicle owner, a family member, or an acquaintance can be stored to prevent the system from issuing warnings when those unique IDs are detected. The unique ID can be registered manually or automatically (learned).

It is also expected that this system will be used in combination with solar panels. As long as the system's solar panels are well powered by a light source, it may not use the low power consumption mode as described above. For example, when solar power is sufficiently generated, all cameras can be turned on regardless of whether they are exterior or interior to the vehicle.

In addition to the combination with solar panels, in the case of vehicles with a charging function, such as plug-in hybrids or EVs, there is no need to switch to the low power consumption mode as described above when it is connected to a charger, since there is no need to worry about the remaining battery power in the vehicle.

This system is not only factory-installed as a genuine product of the car manufacturer, but also offered as an aftermarket product that can be purchased at car accessory stores (meaning Autobacs-like stores in Japan or Autozone store in the US). In that case, the functions could be added to other functional products. For example, if a function is added to existing products, it may be combined with that existing function to improve convenience.

Embodiment 2

Drive Recorder

Figure 2:
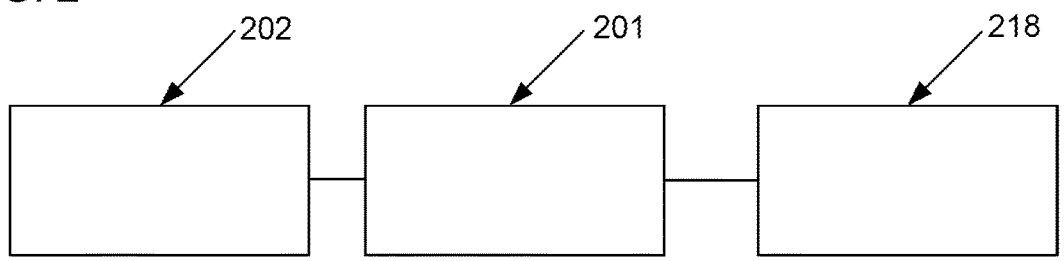
FIG. 2 illustrates a drive recorder operated by a car battery via a camera system in a vehicle.

FIG. 2 illustrates a drive recorder 202 operated under a car battery 218 via a camera system 201. A drive recorder 202 generally outputs high resolution and high-quality images. Power consumption of drive recorder 202 is much higher than that of AI camera used in camera system 201. In combination with camera system 201, it will be possible to reduce the activation time of the drive recorder 202. Specifically, this system increases convenience by turning on and off the power supply 215 in the vehicle to drive recorder 202.

Drive recorder 202 is generally a product that is powered by the vehicle battery (usually 12V in the case of passenger cars), which are turned on automatically at the same time when the vehicle engine is turned on and begin recording automatically when vibration or shock is applied.

Figure 3:
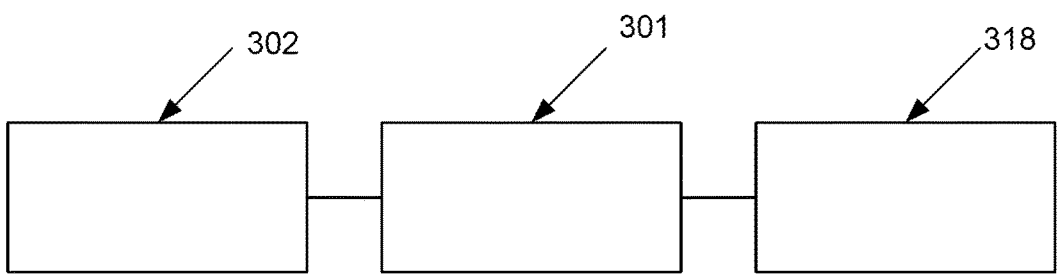
FIG. 3. Illustrates a drive recorder controlled under a camera system including a low power AI camera operated under a car battery in a vehicle.

FIG. 3. illustrates a drive recorder 302 controlled under camera system 301 including a low power AI camera operated under a car battery 318 in a vehicle. As illustrated in FIG. 3, a car battery 318 supplies power to a drive recorder 302 via camera system 301.

Because of high-power consumption of drive recorder 302, drive recorder 302 is arranged not to work while the car is turned off, except immediately after stopping the car. (Most drive recorders are arranged to continue to operate immediately after stopping the car as long as there is an internal battery in the drive recorder, but due to the small capacity of the internal battery, the battery runs out in a matter of minutes and the functions stop, with the battery being recharged the next time the vehicle is turned on).

Since the AI camera system was developed to be used continuously while the car is turned off, power will be supplied to the drive recorder 302 from the car's battery 318 when the software programs determine certain criteria have been met, like recognizing a suspicious person (see above). After that, the system in FIG. 3 will automatically operate based on the specifications of the drive recorder, go into standby mode for vibration detection, and take pictures for a certain period if it detects vibration.

The AI camera system 301 will stop supplying power to the drive recorder 302 when the software program determines certain criteria have been met such as the expiration of a timer or recognizing that the suspicious person has left the area. This allows the drive recorder 302 to be out of vibration detection standby mode while the car is parked, only actively taking pictures when a suspicious person appears, thereby reducing drain on the vehicle battery.

Sound Sensor-Microphone

It is also possible to supplement the recognition accuracy of low-power AI cameras by using the vehicle's AI microphone 112 being a ultra-low power microphone as illustrated in FIG. 1. In this embodiment, since power consumption of the AI microphone 112 is relatively low comparing with AI cameras 102, 104 and 106, it is possible to use AI microphones 112 instead of visual recognition by cameras, or a combination of the two. Recognition using AI microphone also consumes less power than surveillance using AI cameras 102, 104 and 106. Accordingly, the object can be recognized by an AI microphone 112 that has learned to recognize the type of sound (broken window glass, sounds of conversation and periodic breathing in the cabin, the sound rummaging, the cries of children and pets, and the recognition of voice words of people asking for help).

For example, even if an object moving near the vehicle cannot be identified as a bicycle or a motorcycle by the low-resolution camera of the low-power AI camera, it can be identified as a motorcycle by recognizing the engine sound via the AI microphone.

If the vehicle is equipped with multiple AI microphones, the recognition rate can be improved by simultaneously considering the field of view of the AI camera and the directionality of the AI microphones. It is also possible to detect babies, children, or pets left behind by recognizing their sounds, without relying on AI cameras alone. The sounds to be recognized can be identified by learning in advance.

When the low-power AI camera is unable to detect babies or pets left in the cabin, for example when light levels are low such as at night, or when an obstacle has been placed in the way that blocks the camera's view, the $CO_2$ sensor 114 as illustrated in FIG. 1 in the vehicle cabin can be used to determine whether a baby or pet has been left behind based on the amount of change in $CO_2$ concentration (e.g., the $CO_2$ concentration is gradually increasing even though nobody is supposed to be there).

In an environment where multiple low-power AI cameras are installed in a vehicle, if the system determines that it is difficult to recognize an object due to direct sunlight from outside or headlights of other vehicles, the system may activate other equipped normal cameras (which have higher power consumption compared to low-power AI cameras, but which have better recording performance with wide dynamic range and high resolution) may be activated. If the vehicle is one that can be charged, such as an EV or plug-in hybrid, the system may check whether to activate the normal camera, taking into consideration whether the vehicle is being recharged. The same normal camera may be substituted for the one equipped for advanced driver assistance systems (ADAS).

When the camera system recognizes an object (e.g., a car thief, a left-behind baby, a pet, an elderly person, etc.) but determines that the illumination level is too low to take a picture, the system may turn on the car lights (headlights, interior lights, etc.) for a certain period to take the images. The "certain period" can be at the moment of taking an image picture, or it can be kept on for several seconds to several minutes before and after the image is captured.

Although the idea of using low-power AI cameras has been described above, it is possible to use sound recognition (AI microphones) instead of visual recognition by cameras, or a combination thereof. Recognition using AI microphone also consumes less power than surveillance using a regular camera, so the object can be recognized by an AI that has learned the type of sound (broken window glass, sounds of conversation and periodic breathing in a car interior, sounds of rummaging, cries of children and pets, and recognition of voice words of people asking for help). Object recognition accuracy may be improved by combining a low-power AI camera with a low-power AI microphone.

The details and order in which each event occurred may be considered to identify the object, identify the intrusion route, and select the device (including low-power AI camera/microphone) to be activated from the events recognized by the low-power AI camera and low-power AI microphone, respectively. (e.g., only the low-power AI microphone is always activated, and when the sound of breaking glass is heard, all or some of the low-power AI cameras are activated depending on the location of the sound to identify and photograph the type of object, and the server is notified, and the server sends an alert to the car owner's mobile device)

Implementing Anonymous Re-ID Technology

The computer vision system 100 can be further extended by implementing anonymous Re-ID technology being disclosed in U.S. Pat. No. 10,930,145 issued on Feb. 23, 2021. In short, computer programs associated with the camera system 101 illustrated in FIG. 1 assigns anonymous ID to a moving object that passes in front of AI cameras in the camera system 101 with characteristic information, such as a shape, color, etc., of the moving object. In one version the low power AI camera is used as the trigger to capture a single frame from a higher resolution camera 130 than that of the AI camera, upon which to perform re-identification of the person. This saves power by firstly identifying an object as a person by the AI camera, and only then activating the re-ID function with the higher resolution camera 130.

In another version, with increased performance of the underlying processors, re-identification could be moved to AI camera itself for further power savings. By moving more decision-making processes to the AI camera processor, it will eliminate the need to send picture data out to the cloud (a server) as wireless communications often consume many times more power than onboard processing. In both versions, additional external data, including but not limited to, that from other sensors, weather, location and/or events in the area could be incorporated for determining when to activate the re-identification function.

In another embodiment, by using re-ID technology as described in U.S. Pat. No. 10,930,145 issued on Feb. 23, 2021, registered vehicle users could be differentiated from other people. This allows for the vehicle to customize any setting or function it may have based on that re-identification of a registered user versus a non-registered user. For example, if a registered user is re-identified, the vehicle could load a set of customized settings for its in-cabin functions, including but not limited to climate control, lighting, connectivity, as well as other functions outside of the cabin, including but not limited to ride suspension, exterior camera settings, exterior light settings, or powertrain performance settings.

Other functions related to vehicle-security could also be activated based on the re-identification of a non-authorized user. For example, if the non-authorized user is determined to be within a certain distance for a certain amount of time, additional security modes could be activated. Other settings could be controlled if certain scenarios that the AI camera observes deem it necessary, including but not limited to triggering alerts, activating alarms, disabling the vehicle powertrain.

Both of these scenarios can be applied for persons re-identified within the interior of the vehicle as well as the exterior of the vehicle. With the combination of this additional functionality, the overall power consumption of the vehicle can be reduced.

What is claimed is:

1. A computer vision system used for a vehicle comprising:
    a camera system including:
        an AI camera installed in or on the vehicle having a capability of recognizing 1) surrounding environment of the vehicle, 2) moving objects including vehicles in the surrounding environment, and 3) a parking location and a parking direction of the vehicle, and a capability of setting a non-recognition area in the surrounding environment,
        wherein number of the moving objects passing through the non-recognition area are more than a predetermined threshold number in a predetermined period;
    a communication device for communicating data from the computer vison system;
    a controller including software programs for controlling functions of the AI camera and the communication device;
    a battery for supplying power to the camera system; and
    a server designed to communicate with the camera system for processing the data from the camera system via the communication device,
    wherein the software programs include a function for allowing the AI camera to recognize the surrounding environment between the parking location of the vehicle to the nonrecognition area,
    wherein the software programs further include a function for controlling power from the battery to the camera system,
    wherein the software programs include a function for triggering a power save mode of the camera system, and
    wherein the software programs further include a function for turning on or off the AI camera inside and outside the vehicle independently for a predetermined period starting from time an occupant leaves the vehicle.

2. The computer vision system of claim 1,
    wherein the software programs further include a function for turning off a power save mode of the camera system when the AI camera captures a person approaching to the vehicle for a predetermined period or staying within a certain distance from the vehicle for a predetermined period.

3. The computer vision system of claim 1, further comprising:
    a $CO_2$ sensor for measuring $CO_2$ concentration in a cabin of the vehicle, the $CO_2$ sensor being included in the camera system.

4. The computer vision system of claim 3,
    wherein the software programs include a function for monitoring $CO_2$ concentration in a cabin of the vehicle using the $CO_2$ sensor, and
    wherein an alarm signal is sent to a designated person, including but not limited to an owner, of the vehicle when the monitored $CO_2$ concentration is more than a predetermined concentration level.

5. The computer vision system of claim 1, further comprising:
    a drive recorder being linked to the camera system, the drive recorder being controlled by the controller.

6. The computer vision system of claim 5,
    wherein the software programs further include a function for turning on power supply from the battery to the drive recorder via the camera system when the moving object approaches to the vehicle.

7. The computer vision system of claim 5,
    wherein the software programs further include a function for turning on a power supply to the drive recorder via the camera system while a person stays for a certain period within a certain distance of the vehicle.

8. The computer vision system of claim 1, further comprising:
    a camera having a higher resolution than that of the AI camera system,
    wherein the software programs include a function for turning on the camera instead of the AI camera when the AI camera is not able to recognize objects of the AI camera.

9. The computer vision system of claim 1,
    wherein the software programs include a function for turning on a light including a head-light and/or a cabin light of the vehicle for a predetermined time interval when illumination level for recognizing objects in the vehicle or outside of the vehicle is less than a predetermined level.

10. The computer vision system of claim 1, further comprising:
    an AI microphone for capturing sound generated by the moving objects, the AI microphone installed in the vehicle having a capability of recognizing 1) the surrounding environment, and 2) the moving objects including vehicles and or people passing through a parking location of the vehicle by using captured sound generated by the moving objects and or the surrounding environment.

11. The computer vision system of claim 10,
    wherein the software programs include a function for turning power on with the AI camera or the AI microphone nearby an event captured by the AI microphones when the AI microphone captures sound signals generated by the event, recognizes contents of the event and order in which the event occurs, sends information including the contents of the event and the order thereof to the server so that the server sends a notification to a designated person or system, including an owner of the vehicle.

12. The computer vision system of claim 1, further comprising:
a camera having a higher resolution than that of the AI camera, the camera being linked to the controller,
wherein the software programs further include functions for allowing the camera to start to capture images of the objects to perform re-identification of one of the objects.

13. The computer vision system of claim 12,
wherein the software programs further include a function for giving decision-making process including a set of customized settings for its in-cabin functions, climate control and lighting to the AI camera.

14. The computer vision system of claim 12,
wherein the software programs further include a function for activating security system of the vehicle based on the re-identification when non-authorized person is determined to be within a certain distance from the vehicle.

15. A computer vision system used for a vehicle comprising:
a camera system including:
an AI camera installed in or on the vehicle having a capability of recognizing 1) surrounding environment of the vehicle, 2) moving objects including vehicles in the surrounding environment, and 3) a parking location and a parking direction of the vehicle, and a capability of setting a non-recognition area in the surrounding environment,
wherein number of the moving objects passing through the non-recognition area are more than a predetermined threshold number in a predetermined period;
a communication device for communicating data from the computer vison system;
a controller including software programs for controlling functions of the AI camera and the communication device;
a battery for supplying power to the camera system; and
a server designed to communicate with the camera system for processing the data from the camera system via the communication device,
wherein the software programs include a function for allowing the AI camera to recognize the surrounding environment between the parking location of the vehicle to the nonrecognition area, and
wherein the software programs further include a function for controlling power from the battery to the camera system,
said computer vision system further comprising a satellite positioning system for detecting a parking location and a parking direction, the satellite positioning system being linked to the controller,
wherein data from the satellite positioning system is used as initial data of a location where the vehicle is parked, and
wherein the software programs further include a function for checking whether there is data including the same parking location and parting direction in a past, then turning off power supply from the battery to the AI camera when there is the same data and the AI camera cannot recognize any one of surrounding environment, moving objects and a parking location of the vehicle.

* * * * *